US00PP35173P2

(12) United States Plant Patent
Horvath

(10) Patent No.: US PP35,173 P2
(45) Date of Patent: May 16, 2023

(54) ***EUPATORIUM PERFOLIATUM* PLANT NAMED 'BLIND DATE'**

(50) Latin Name: *Eupatorium perfoliatum*
Varietal Denomination: Blind Date

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/803,793

(22) Filed: Nov. 28, 2022

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Karen M Redden

(57) ABSTRACT

A new and distinct variety of *Eupatorium perfoliatum* 'Blind Date' plant as illustrated and described, characterized by the combination larger and darker colored foliage, taller height, and more vigorous plants compared to the seed parent.

1 Drawing Sheet

Figure 1:
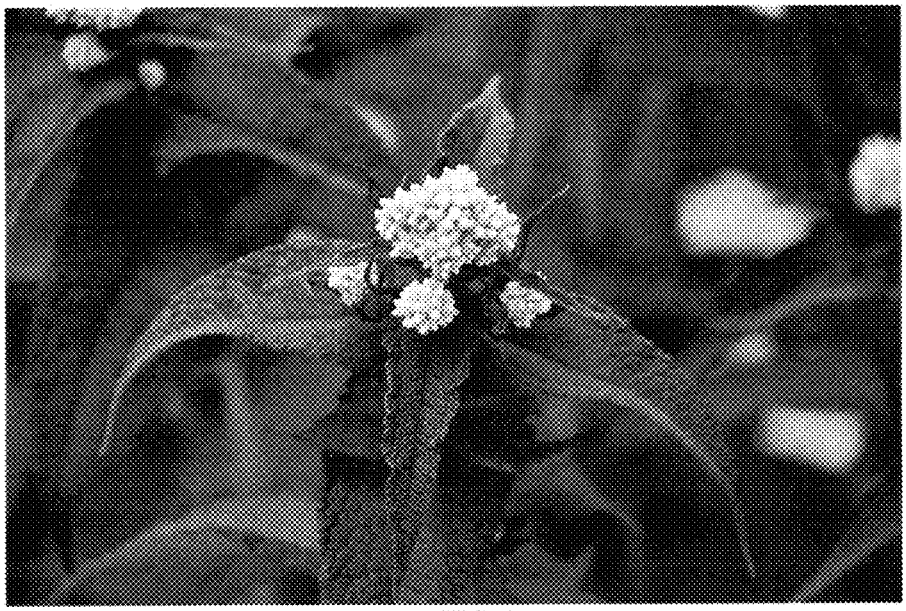

Latin name: *Eupatorium perfoliatum.*
Cultivar name: 'Blind Date'.

BACKGROUND OF THE INVENTION

The present invention relates to a new and distinct hybrid of *Eupatorium perfoliatum* plant named 'Blind Date' characterized by the combination of larger and darker colored foliage, taller height, and more vigorous plants compared to the seed parent. The new *Eupatorium perfoliatum* was raised as a seedling from open pollinated seed sown from the seed parent *Eupatorium perfoliatum* 'Milk and Cookies' plant, not patented, in Hebron, Ill. in 2018. The selection of the new plant was due to its' larger and darker colored foliage, taller height, and more vigorous plants compared to the seed parent. Initial asexual reproduction has taken place at a nursery in Hebron, Ill. since 2019 by means of stem cuttings. The new *Eupatorium perfoliatum* has shown to be stable and identical in reproduction after rooting over 600 plants from 2019 to 2021. No plants of the new *Eupatorium perfoliatum* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Eupatorium perfoliatum* plant named 'Blind Date' characterized by the combination of larger and darker colored foliage, taller height, and more vigorous plants compared to the seed parent.

SUMMARY OF THE INVENTION

The new *Eupatorium perfoliatum* plant named 'Blind Date' characterized by the combination larger and darker colored foliage, taller height, and more vigorous plants compared to the seed parent have been observed to be unique and stable.

Plants of the new *Eupatorium perfoliatum* can be compared to plants of *Eupatorium perfoliatum* 'Milk and Cookies' the seed parent, not patented. The new *Eupatorium perfoliatum* plant has a mature size measuring 120 cm high and 75 cm wide while *Eupatorium perfoliatum* 'Milk and Cookies' measures 100 cm high and 65 cm wide. The new *Eupatorium perfoliatum* plant has larger foliage approximately 11 cm long and 4 cm wide while *Eupatorium perfoliatum* 'Milk and Cookies' has foliage that reaches approximately 8 cm long and 3 cm wide. The new *Eupatorium perfoliatum* plant has darker foliage color of 187 B while *Eupatorium perfoliatum* 'Milk and Cookies' has foliage colored 60 A.

Plants of the new *Eupatorium perfoliatum* can also be compared to the typical species of unnamed *Eupatorium perfoliatum* not patented. The new *Eupatorium perfoliatum* plant has darker foliage color of 187 B while typical species of unnamed *Eupatorium perfoliatum* has green foliage color of 146 A.

Plants of the new *Eupatorium perfoliatum* can also be compared to the *Eupatorium rugosum* not patented. The new *Eupatorium perfoliatum* plant has darker foliage color of 187 B while *Eupatorium rugosum* has green foliage color of 137 A. The new *Eupatorium perfoliatum* plant has rugose foliage while *Eupatorium rugosum* has glabrous.

DESCRIPTION OF PHOTOGRAPHS

Figure 2:
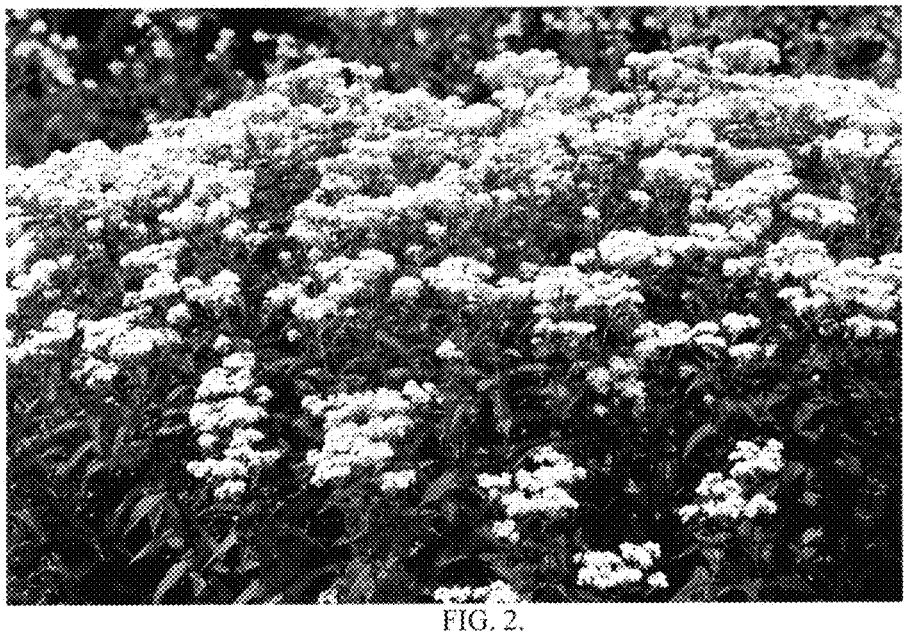

FIG. 1. A budded stem on a 2 year old plant in July.
FIG. 2. A flowering plant in August.

DETAILED BOTANICAL DESCRIPTION

In the following description, color references are made to The Royal Horticultural Society Colour Chart 2001 edition. Plants used for the description were grown for two seasons at a nursery in Hebron, Ill. Measurements and numerical values represent averages of typical plants.

Botanical classification: *Eupatorium perfoliatum* 'Blind Date'.

Parentage: Male or pollen parent an unknown *Eupatorium*, female or seed parent, *Eupatorium perfoliatum* 'Milk and Cookies'.

Propagation: Vegetative division and stem cutting propagation.

Root description: Fibrous, thin thickness, white in color.

Root habit: Moderate branching, moderate density.

Plant description: Herbaceous perennial. Overall habit of the new *Eupatorium perfoliatum* is an upright clump, with branching stems topped by white inflorescences starting in August.

*Plant height.*—120 cm.
*Plant width.*—75 cm.
*Primary stem diameter.*—9 mm.
*Primary and secondary stem description.*—Branching, with 20 or more leaves per secondary stem. Leaves get smaller as they go up the stem. Strength — strong.
*Primary and lateral stem texture.*—Rugose with shorts stiff hairs 1-2 mm in length.
*Secondary stem description.*—Average 10 lateral stems per primary stem.
*Secondary stem length.*—60 cm.
*Secondary stem diameter.*—5 mm.
*Secondary stem internodes.*—5 cm.
*Stem color.*—187 B.

Foliage:

*Type.*—Herbaceous, simple.
*Leaf arrangement.*—Connate, perfoliate.
*Length.*—11 cm.
*Width.*—4 cm.
*Shape.*—Lanceolate.
*Apex.*—Acuminate.
*Base.*—Truncate, fused around the stem at times.
*Margin.*—Dentate.
*Adaxial texture.*—Glabrous. Abaxial Texture — rugose with shorts stiff hairs 1-2 mm in length.
*Venation.*—Arcuate. Spring Venation Color — 186 D; Summer Venation Color — 137 A.
*Adaxial leaf description.*—Spring color is 187 B including developing, fully expanded. Summer color is 137 A. Fall color is 59 A.
*Abaxial leaf description.*—Spring color is 187 B including developing, fully expanded. Summer color is 137 B. Fall color is 59 A.

Bud:

*Bud shape.*—Oblong.
*Bud length.*—7 mm.
*Bud diameter.*—7 mm.
*Bud color.*—155 C.

Inflorescence:

*Inflorescence type.*—Cymose panicle of composite inflorescences comprised of disc florets on branched flowering stems.
*Position.*—Borne on both terminal and axillary peduncles above the foliage.
*Number of inflorescences per plant.*—Approximately 7000.
*Arrangement.*—Disc florets.
*Mature center disc.*—5 mm wide and 5 mm height.
*Number of disc florets.*—13.
*Immature disc floret color.*—Close to 155 C.
*Mature disc floret color.*—Close to N155 C.
*Disc floret diameter.*—1 mm or less at apex, less than 1 mm at base.
*Disc floret shape.*—Tubular, corolla is fused.
*Disc floret length.*—6 mm.
*Disc floret width.*—1 mm.
*Disc floret apex.*—Acute.
*Disc floret margin.*—Entire.
*Disc floret count.*—15-20.
*Overall inflorescence size.*—16 cm or more across in diameter with disc florets, 26 cm in height.
*Bloom period and duration.*—August into September. 4-6 weeks on the plant.
*Blooming habit.*—Upright on 120 cm terminal flowering stems.

Phyllaries:

*Number of phyllaries per inflorescence.*—10 average.
*Length.*—6 mm.
*Width.*—1 mm.
*Shape.*—Lanceolate.
*Apex.*—Mucronate.
*Base.*—Fused.
*Margin.*—Entire.
*Texture.*—Both upper and lower surface glabrous.
*Color.*—Adaxial 155 C and Abaxial 155 C.

Peduncles:

*Length.*—Of both terminal 30 cm and axillary peduncles 15 cm.
*Diameter.*—Of both terminal 5 mm and axillary peduncles 4 mm.
*Angle.*—Erect to about 15 degrees from vertical.
*Strength.*—Strong, Texture — pubescent, Color — 187 B.

Reproductive organs:

*Androecium.*—Quantity per disc floret, 5.
*Filament length.*—5 mm.
*Filament color.*—155 B.
*Anther shape.*—Oblong.
*Anther length.*—1 mm.
*Anther color.*—Close to 155 C.
*Pollen amount.*—Moderate.
*Gynoecium present on disc florets.*—
*Pistils.*—One, length 5 mm, width less than 1 mm.
*Stigma shape.*—Lanceolate, Stigma color — 8 A.
*Style.*—Bifurcate, exserted. Length — 6 mm, Style color — 155 D.
*Scent.*—No scent noticed.

Seed and fruit: Achenes, Length — 2 mm. Color — 200 A.

Disease resistance: Resistance to diseases common to *Eupatorium perfoliatum* has not been observed on plants grown under nursery conditions.

Hardiness: Plants of the new *Eupatorium perfoliatum* have been observed to be hardy to USDA Zone 5.

I claim:

1. A new and distinct variety of *Eupatorium perfoliatum* 'Blind Date' plant as illustrated and described, characterized by the combination larger and darker colored foliage, taller height, and more vigorous plants compared to the seed parent.

* * * * *